United States Patent [19]
Crooks et al.

[11] Patent Number: 5,616,707
[45] Date of Patent: Apr. 1, 1997

[54] COMPOUNDS WHICH ARE USEFUL FOR PREVENTION AND TREATMENT OF CENTRAL NERVOUS SYSTEM DISORDERS

[76] Inventors: Peter A. Crooks, 3233 Raven Cir., Lexington, Ky. 40502; William S. Caldwell, 1270 Yorkshire Rd., Winston-Salem, N.C. 27106; Gary M. Dull, 1175 Sequoia Dr., Lewisville, N.C. 27023; Balwinder S. Bhatti, 605 Elk Lake Dr., Lexington, Ky. 40517; Niranjan M. Deo, 2150 Richmond Rd., Apt. #7, Lexington, Ky. 40502; Alain Ravard, 700 Woodland Ave., #B 211, Lexington, Ky. 40508

[21] Appl. No.: 364,976

[22] Filed: Jan. 6, 1995

[51] Int. Cl.⁶ .................... C07D 237/02; C07D 213/02
[52] U.S. Cl. ............................................ 544/242; 546/329
[58] Field of Search ............................. 544/242; 546/329

[56] References Cited

U.S. PATENT DOCUMENTS

| | | | |
|---|---|---|---|
| 4,786,646 | 11/1988 | Guthrie et al. | 514/346 |
| 4,916,145 | 4/1990 | Tilley et al. | 514/357 |
| 4,922,901 | 5/1990 | Brooks et al. | 128/203.26 |
| 4,927,838 | 5/1990 | Guthrie et al. | 514/337 |
| 5,210,076 | 5/1993 | Berliner et al. | 514/21 |
| 5,212,188 | 5/1993 | Caldwell et al. | 514/343 |
| 5,227,391 | 7/1993 | Caldwell | 514/343 |

FOREIGN PATENT DOCUMENTS

| | | | |
|---|---|---|---|
| 215297 | 8/1986 | European Pat. Off. | 564/129 |

OTHER PUBLICATIONS

Kotyarevsku et al, Chemical Abstracts, vol. 71, No. 16, Abstract No. 81, 101z, Oct. 20, 1969, p. 368.
Kurbanov et al, Chemical Abstracts, vol. 109, No. 25, Abstract No. 230,750☆, Dec. 19, 1988, p. 834.
Soed et al, Agri Biol. Chem, 1968, vol. 32(6), pp. 747–752.
Chemical Abstracts vol. 97, No. 1, Abstract No. 6167j pp. 596–597, Jul. 5, 1982.
Chemical Abstracts vol. 78, No. 25, Abstract No. 159952u, p. 445, Jun. 25, 1973.
Acheson, R. et al., *J. Chem. Soc. Perkin Trans.*, vol. 2, pp. 579–585 (1980).
Erdtman, H. et al., *Acta Chem. Scand.*, vol. 17, pp. 1717–1726 (1963).
Frank, W. et al., *J. Org. Chem.*, vol. 43(15), pp. 2947–2949 (1978).
Gol'dfarb, Y. et al., *J. Gen. Chem.*, USSR(Engl. Transl.) vol. 39, pp. 1071–1075 (1969).
Kamimura, H. et al., *Agr. Biol. Chem.*, vol. 27, No. 10, pp. 684–688 (1963).
LaForge, F., *JACS*, vol. 50, pp. 2477–2483 (1928).
Malek, N. et al., *J. Org. Chem.*, vol. 47, pp. 5395–5397 (1982).
Rondahl, L., *Acta Pharm. Suec.*, vol. 14, No. 2, pp. 113–118 (1977).
Rondahl, L., *Acta Pharm. Suec.*, vol. 13, pp. 229–234 (1976).
Sprouse, C. et al., Abstracts of Papers, p. 32, Coresta/TCRC, Joint Conference (1972).
Ashimori, A. et al., *Chem. Pharm. Bull.* vol. 38(9), pp. 2446–2458 (1990).

*Primary Examiner*—Zinna Northington Davis

[57] ABSTRACT

Patients susceptible to or suffering from central nervous system disorders are treated by administering an effective amount of an aryl substituted olefinic amine compound or an aryl substituted acetylenic compound. Exemplary compounds are (E)-N-methyl-4-[3-(6-methylpyridin)yl]-3-butene-1-amine and N-methyl-4-(3-pyridinyl)-3-butyne-1-amine.

6 Claims, No Drawings

12 COMPOUNDS WHICH ARE USEFUL FOR PREVENTION AND TREATMENT OF CENTRAL NERVOUS SYSTEM DISORDERS

BACKGROUND OF THE INVENTION

The present invention relates to compounds having pharmaceutical properties, and in particular, to compounds useful for preventing and treating central nervous system (CNS) disorders. The present invention relates to a method for treating patients suffering from or susceptible to such disorders, and in particular, to a method for treating patients suffering from those disorders which are associated with neurotransmitter system dysfunction. The present invention also relates to compositions of matter useful as pharmaceutical compositions in the prevention and treatment of CNS disorders which have been attributed to neurotransmitter system dysfunction.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic deficiency, a dopaminergic deficiency, an adrenergic deficiency and/or a serotonergic deficiency. CNS disorders of relatively common occurrence include presenile dementia (early onset Alzheimer's disease), senile dementia (dementia of the Alzheimer's type). Parkinsonism including Parkinson's disease. Huntington's chorea, tardive dyskinesia, hyperkinesia, mania, attention deficit disorder, anxiety, dyslexia, schizophrenia and Tourette's syndrome.

Senile dementia of the Alzheimer's type (SDAT) is a debilitating neurodegenerative disease mainly afflicting the elderly; characterized by a progressive intellectual and personality decline, as well as a loss of memory, perception, reasoning, orientation and judgment. One feature of the disease is an observed decline in the function of cholinergic systems, and specifically, a severe depiction of cholinergic neurons (i.e., neurons that release acetylcholine, which is believed to be a neurotransmitter involved in learning and memory mechanisms). See, Jones, et al., *Intern. J. Neurosci.*, Vol. 50, p. 147 (1990); Perry, *Br. Med. Bull.*, Vol. 42, p. 63 (1986) and Sitaram, et al., *Science*, Vol. 201, p. 274 (1978). It has been observed that nicotinic acetylcholine receptors, which bind nicotine and other nicotinic agonists with high affinity, are depleted during the progression of SDAT. See, Giacobini, *J. Neurosci. Res;*, Vol. 27, p. 548 (1990); and Baron, *Neurology*, Vol. 36, p. 1490 (1986). As such, it would seem desirable to provide therapeutic compounds which either directly activate nicotinic receptors in place of acetylcholine or act to minimize the loss of those nicotinic receptors.

Certain attempts have been made to treat SDAT. For example, nicotine has been suggested to possess an ability to activate nicotinic cholinergic receptors upon acute administration, and to elicit an increase in the number of such receptors upon chronic administration to animals. See, Rowell, *Adv. Behav. Biol.*, Vol. 31, p. 191 (1987); and Marks, *J. Pharmacol. Exp. Ther.*, Vol. 226, p. 817 (1983). It also has been proposed that nicotine can act directly to elicit the release of acetylcholine in brain tissue, to improve cognitive functions, and to enhance attention. See, Rowell, et al., *J. Neurochem.*, Vol. 43, p. 1593 (1984); Sherwood, *Human Psychopharm.*, Vol. 8, pp. 155–184 (1993); Hodges, et al., *Bio. of Nic.*, Edit. by Lippiello, et al., p. 157 (1991); Sahakian, et al., *Br. J. Psych.*, Vol. 154, p. 797 (1989); and U.S. Pat. No. 4,965,074 to Leeson and U.S. Pat. No. 5,242,935 to Lippiello et al. Other methods for treating SDAT have been proposed, including U.S. Pat. No. 5,212, 188 to Caldwell et al. and U.S. Pat. No. 5,227,391 to Caldwell et al. and European Patent Application No. 588, 917. Another proposed treatment for SDAT is Cognex, which is a capsule containing tacrine hydrochloride, available from Parke-Davis Division of Warner-Lambert Company, which reportedly preserves existing acetylcholine levels in patients treated therewith.

Parkinson's disease (PD) is a debilitating neurodegenerative disease, presently of unknown etiology, characterized by tremors and muscular rigidity. A feature of the disease appears to involve the degeneration of dopaminergic neurons (i.e., which secrete dopamine). One symptom of the disease has been observed to be a concomitant loss of nicotinic receptors which are associated with such dopaminergic neurons, and which are believed to modulate the process of dopamine secretion. See, Rinne, et al., *Brain Res.*, Vol. 54, pp. 167–170 (1991) and Clark. et al., *Br. J. Pharm.*, Vol. 85, pp. 827–835 (1985). It also has been proposed that nicotine can ameliorate the symptoms of PD. See, Smith et al., *Rev. Neurosci.*, Vol. 3(1), pp. 25–43 (1982).

Certain attempts have been made to treat PD. One proposed treatment for PD is Sinemet CR, which is a sustained-release tablet containing a mixture of carbidopa and levodopa, available from The DuPont Merck Pharmaceutical Co. Another proposed treatment for PD is Eldepryl, which is a tablet containing selefiline hydrochloride, available from Somerset Pharmaceuticals, Inc. Another proposed treatment for PD is Parledel, which is a tablet containing bromocriptine mesylate, available from Sandoz Pharmaceuticals Corporation. Another method for treating PD and a variety of other neurodegenerative diseases has been proposed in U.S. Pat. No. 5,210,076 to Berliner et al.

Tourette's syndrome (TS) is an autosomal dominant neuropsychiatric disorder characterized by a range of neurological and behavioral symptoms. Typical symptoms include (i) the onset of the disorder before the age of 21 years, (ii) multiple motor and phonic tics although not necessarily concurrently, (iii) variance in the clinical phenomenology of the tics, and (iv) occurrence of quasi daily tics throughout a period of time exceeding a year. Motor tics generally include eye blinking, head jerking, shoulder shrugging and facial grimacing; while phonic or vocal tics include throat clearing, sniffling, yelping, tongue clicking and uttering words out of context. The pathophysiology of TS presently is unknown, however it is believed that neurotransmission dysfunction is implicated with the disorder. See, Calderon-Gonzalez et al., *Intern. Pediat.*, Vol. 8(2), pp. 176–188 (1993) and *Oxford Textbook of Medicine*, Eds. Weatherall et al., Chapter 21.218 (1987).

It has been proposed that nicotine pharmacology is beneficial in suppressing the symptoms associated with TS. See, Devor et al., *The Lancet*, Vol. 8670, p. 1046 (1989); Jarvik, *British J. of Addiction*, Vol. 86, pp. 571–575 (1991); McConville et al. *Am. J. Psychiatry*, Vol. 148 (6), pp. 793–794 (1991); Newhouse et al., *Brit. J. Addic.*, Vol. 86, pp. 521–526 (1991); McConville et al., *Biol. Psychiatry, Vol.* 31, pp. 832–840 (1992); and Sanberg et al., *Proceedings from Intl. Symp. Nic.,* S39 (1994). It also has been proposed to treat TS using Haldol, which is haloperidol available from McNeil Pharmaceutical; Catapres, which is clonidine available from Bochringer Ingelheim Pharmaceuticals, Inc., Orap, which is pimozide available from Gate Pharmaceuticals; Prolixin, which is fluphenazine available from Apothecon Division of Bristol-Myers Squibb Co.; and Klonopin, which is clonazepam available from Hoffmann-LaRoche Inc.

Attention deficit disorder (ADD) is a disorder which affects mainly children, although ADD can affect adolescents and adults. See, Vinson, *Arch. Fam. Med.,* Vol. 3(5), pp. 445–451 (1994); Hechtman, *J. Psychiatry Neurosci.,* Vol. 19 (3), pp. 193–201 (1994); Faraone et al., *Biol. Psychiatry,* Vol. 35(6), pp. 398–402 (1994) and Malone et al., *J. Child Neurol.,* Vol. 9(2), pp. 181–189 (1994). Subjects suffering from the disorder typically have difficulty concentrating, listening, learning and completing tasks; and are restless, fidgety, impulsive and easily distracted. Attention deficit disorder with hyperactivity (ADHD) includes the symptoms of ADD as well as a high level of activity (e.g., restlessness and movement). Attempts to treat ADD have involved administration of Dexedrine, which is a sustained release capsule containing dextroamphetamine sulfate, available from SmithKline Beecham Pharmaceuticals; Ritalin, which is a tablet containing methylphenidate hydrochloride, available from Ciba Pharmaceutical Company; and Cylert, which is a tablet containing premoline, available from Abbott Laboratories. In addition, it has been reported that administration of nicotine to an individual improves that individual's selective and sustained attention. See, Warburton et al., *Cholinergic control of cognitive resources, Neuropsychobiology,* Eds. Mendlewicz, et al., pp 43–46 (1993).

Schizophrenia is characterized by psychotic symptoms including delusions, catatonic behavior and prominent hallucinations, and ultimately results in a profound decline in the psychosocial affect of the subject suffering therefrom. Traditionally, schizophrenia has been treated with Klonopin, which is available as a tablet containing clonazepam, available from Hoffmann-LaRoche Inc.; Thorazine, which is available as a tablet containing chlorpromazine, available from SmithKline Beecham Pharmaceuticals; and Clozaril, which is a tablet containing clozapine, available from Sandoz Pharmaceuticals. Such neuroleptics are believed to be effective as a result of interaction thereof with the dopaminergic pathways of the CNS. In addition, a dopaminergic disfunction possessed by individuals suffering from schizophrenia has been proposed. See, Lieberman et al., *Schizophr. Bull.,* Vol. 19, pp. 371–429 (1993) and Glassman, *Amer. J. Psychiatry,* Vol. 150, pp. 546–553 (1993). Nicotine has been proposed as being effective in effecting neurotransmitter dysfunction associated with schizophrenia. See, Merriam et al., *Psychiatr. Annals,* Vol. 23, pp. 171–178 (1993) and Adler et al., *Biol. Psychiatry,* Vol. 32, pp. 607–616 (1992).

Nicotine has been proposed to have a number of pharmacological effects. Certain of those effects may be related to effects upon neurotransmitter release. See, for example, Sjak-shie et al., *Brain Res.,* Vol. 624, pp. 295–298 (1993), where neuroprotective effects of nicotine are proposed. Release of acetylcholine and dopamine by neurons upon administration of nicotine has been reported by Rowell et al., *J. Neurochem.,* Vol. 43, pp. 1593–1598 (1984); Rapier et al., *J. Neurochem.,* Vol. 50, pp. 1123–1130 (1988); Sandor et al., *Brain Res.,* Vol. 567, pp. 313–316 (1991) and Vizi, *Br. J. Pharmacol.,* Vol. 47, pp. 765–777 (1973). Release of norepinephrine by neurons upon administration of nicotine has been reported by Hall et al., *Biochem. Pharmacol.,* Vol. 21, pp. 1829–1838 (1972). Release of serotonin by neurons upon administration of nicotine has been reported by Hery et al., *Arch. Int. Pharmacodyn. Ther.,* Vol. 296, pp. 91–97 (1977). Release of glutamate by neurons upon administration of nicotine has been reported by Toth et al., *Neurochem Res.,* Vol. 17, pp. 265–271 (1992). Therefore, it would be desirable to provide a pharmaceutical composition containing an active ingredient having nicotinic pharmacology, which pharmaceutical composition is capable of illicting neurotransmitter release within a subject in order to prevent or treat a neurological disorder. In addition, nicotine reportedly potentiates the pharmacological behavior of certain pharmaceutical compositions used for the treatment of certain CNS disorders. See, Sanberg et al., *Pharmacol. Biochem. & Behavior,* Vol. 46, pp. 303–307 (1993); Harsing et al., *J. Neurochem.,* Vol. 59, pp. 48–54 (1993) and Hughes, *Proceedings from Intl. Symp. Nic,* S40 (1994). Furthermore, various other beneficial pharmacological effects of nicotine have been proposed. See, Decina et al., *Biol. Psychiatry,* Vol. 28, pp. 502–508 (1990); Wagner et al., *Pharmacopsychiatry,* Vol. 21, pp. 301–303 (1988); Pomerleau et al., *Addictive Behaviors,* Vol. 9, p. 265 (1984); Onaivi et al., *Life Sci.,* Vol. 54(3), pp. 193–202 (1994) and Hamon, *Trends in Pharmacol. Res.,* Vol. 15, pp. 36–39.

It would be desirable to provide a useful method for the prevention and treatment of a CNS disorder by administering a nicotinic compound to a patient susceptible to or suffering from such a disorder. It would be highly beneficial to provide individuals suffering from certain CNS disorders with interruption of the symptoms of those diseases by the administration of a pharmaceutical composition which has nicotinic pharmacology and which has a beneficial effect upon the functioning of the CNS, but which does not provide any significant associated side effects (e.g., increased heart rate and blood pressure) attendant with interaction of that compound with cardiovascular sites. It would be highly desirable to provide a pharmaceutical composition incorporating a compound which interacts with nicotinic receptors which have the potential to affect the functioning of the CNS, but which does not significantly affect those receptors which have the potential to induce undesirable side effects (e.g., appreciable pressor cardiovascular effects and appreciable activity at skeletal muscle sites).

SUMMARY OF THE INVENTION

The present invention relates to aryl substituted aliphatic amine compounds, aryl substituted olefinic amine compounds and aryl substituted acetylenic amine compounds.

The present invention relates to a method for providing prevention or treatment of a central nervous system (CNS) disorder. The method involves administering to a subject an effective amount of a compound of the present invention.

The present invention in another aspect, relates to a pharmaceutical composition comprising an effective amount of a compound of the present invention. Such a pharmaceutical composition incorporates a compound which has the capability of interacting with relevant nicotinic receptor sites of a subject, and hence has the capability of acting as a therapeutic in the prevention or treatment of a CNS disorder.

The pharmaceutical compositions of the present invention are useful for the prevention and treatment of CNS disorders. The pharmaceutical compositions provide therapeutic benefit to individuals suffering from certain CNS disorders and exhibiting clinical manifestations of such disorders in that the compounds within those compositions have the potential to (i) exhibit nicotinic pharmacology and affect nicotinic receptors sites in the CNS (e.g., act as a pharmacological agonist to activate nicotinic receptors), and (ii) elicit neurotransmitter secretion, and hence prevent and suppress the symptoms associated with those diseases. In addition, the compounds are expected to have the potential to (i) increase the number of nicotinic cholinergic receptors of the brain of the patient, (ii) exhibit neuroprotective effects and (iii) not provide appreciable adverse side effects (e.g., significant increases in blood pressure and heart rate, and significant effects upon skeletal muscle). The pharmaceutical compositions of the present invention are believed to be safe and effective with regards to prevention and treatment of CNS disorders.

DETAILED DESCRIPTION OF THE PREFERRED EMBODIMENTS

The present invention, in one aspect, relates to certain compounds having the formula:

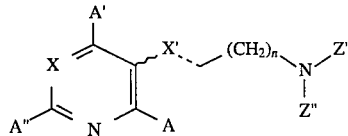

where X is nitrogen or carbon bonded to a substituent species characterized as having a sigma m value greater than 0, often greater than 0.1, generally greater than 0.2 and even greater than 0.3; less than 0 and generally less than −0.1; or 0; as determined in accordance with Hansch et al., *Chem. Rev.*, Vol. 91, pp. 165–195 (1991); n is an integer which can range from 1 to 5, preferably from 1 to 3, and most preferably is 2 or 3; Z' and Z" individually represent hydrogen or lower alkyl (e.g., alkyl containing one to five carbon atoms, such as methyl, ethyl or isopropyl), and preferably at least one of Z' and Z" is hydrogen; A, A' and A" individually represent hydrogen, alkyl (e.g., lower straight chain or branched alkyl, including $C_1$–$C_7$, but preferably methyl or ethyl) or halo (e.g., F, Cl, Br or I); the dashed line in the structure represents a C—C single bond, a C—C double bond or a C—C triple bond; the wavy line in the structure represents a cis (Z) or trans (E) form of the compound when the dashed line is a C—C double bond; and X' represents $CH_2$ when the dashed line is a C—C single bond, CH when the dashed line is a C—C double bond, and C when the dashed line is a C—C triple bond. X includes N, C—H, C—F, C—Cl, C—Br, C—I, C—NR'R", C—$CF_3$, C—OH, C—CN, C—SH, C—$SCH_3$, C—$N_3$, CSO:$CH_3$, C—OR', C—C(=O)N R'R", C—NR'C(=O)R', C—C(=O)OR', C—OC(=O)R', C—OC(=O)NR'R" and C—NR'C(=O)OR' where R' and R" are individually hydrogen or lower alkyl (e.g., alkyl containing one to five carbon atoms, preferably methyl or ethyl). When X represents a carbon atom bonded to a substituent species, that substituent species often has a sigma m value which is between about −0.3 and about 0.75, and frequently between about −0.25 and about 0.6. In certain circumstances when X represents a carbon atom bonded to a substituent species, the dashed line is a C—C double bond and the compound has the trans (E) form, the substituent species is characterized as having a sigma m value not equal to 0. Particularly when the dashed line is a C—C double bond, the compound has the trans (E) form. A, A', A" and Z' all are hydrogen, n is 2, and Z" is methyl, the substituent species is characterized as having a sigma m value not equal to 0. In addition, it is highly preferred that A is hydrogen, it is preferred that A' is hydrogen, and normally A" is hydrogen. Generally, both A and A' are hydrogen; sometimes A and A' are hydrogen, and A" is methyl or ethyl; and often A, A' and A" are all hydrogen. One representative compound is N-methyl-4-(3-pyridinyl)-butane-1-amine for which for which the dashed line is a C—C single bond, X' is $CH_2$, X is C—H, n is 2, and A, A', A" and Z' each are hydrogen, and Z" is methyl. Another representative compound is N-methyl-4-(3-pyridinyl)-3-butyne-1-amine for which for which the dashed line is a C—C triple bond, X' is C, X is C—H, n is 2, and A, A', A" and Z' each are hydrogen, and Z" is methyl. Other representative compounds are (Z)-metanicotine and (E)-metanicotine, for which the dashed line is a C—C double bond, X' is CH, n is 2, and A, A', A" and Z' each are hydrogen, and Z" is methyl. Of particular interest are compounds having the formula:

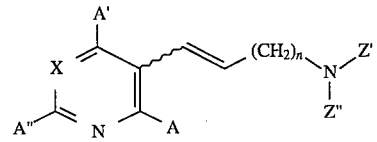

where n, X, A, A', A", Z' and Z" are as defined hereinbefore, and those compounds can have the cis (Z) or trans (E) form. For such compounds of particular interest, X most preferably is nitrogen or carbon bonded to a substituent species characterized as having a sigma m value greater than 0, often greater than 0.1, generally greater than 0.2 and even greater than 0.3; less than 0 and generally less than −0.1; or 0. One representative compound is (E)-4-(5-pyrimidinyl)-3-butene-1-amine for which X is N, n is 2, and A, A', A", Z' and Z" each are hydrogen. Another representative compound is (E)-4-[3-(5-methoxypridin)yl]-3-butene-1-amine for which X is C—$OCH_3$, n is 2, and A, A', A", Z' and $Z^{41}$ each are hydrogen. Another representative compound is (E)-N-methyl-4-(5-pyrimidinyl)-3-butene-1-amine for which X is N, n is 2, A, A', A", and Z' are each hydrogen, and Z" is methyl. Another representative compound is (E)-N-methyl-4-[3-(5-methoxpyridin)yl]-3-butene-1-amine for which X is C—$OCH_3$, n is 2, and A, A', A", and Z' are each hydrogen, and Z" is methyl. Another representative compound is (E)-4-[3-(5-ethoxypyridin)yl]-3 -butene-1-amine for which X is C—$OCH_2CH_3$, n is 2, and A, A', A", Z' and Z" each are hydrogen. Another representative compound is (E)-N-methyl-4-[3-(5-ethoxylpyridin)yl]-3-butene-1-amine for which X is C—$OCH_2CH_3$, n is 2, A, A', A" and Z' each are hydrogen, and Z" is methyl. Another representative compound is (E)-4-[3-(5-aminopyridin)yl]-3-butene-1-amine for which X is C—$NH_2$, n is 2, and A, A', A", Z' and Z" each are hydrogen. Another representative compound is (E)-N-methyl-4-[3-(5-aminopyridin)yl]-3-butene-1-amine for which X is C—$NH_2$, n is 2, A, A', A" and Z' each are hydrogen, and Z" is methyl. Another representative compound is (E)-4-[3-(5-bromopyridin)yl]-3-butene-1-amine for which X is C—Br, n is 2, and A, A', A", Z' and Z" each are hydrogen. Another representative compound is (E)-N-methyl-4-[3-(5-bromopyridin)yl]-3-butene-1-amine for which X is C—Br, n is 2, A, A', A" and Z' each are hydrogen, and Z" is methyl. Another representative compound is (E)-4-[3-(5-methoxy-6-methylpyridin)yl]-3-butene-1-amine for which X is C—$OCH_3$, n is 2, A" is methyl, and A, A', Z' and Z" each are hydrogen. Another representative compound is (E)-N-methyl-4-[3-(5-methoxy-6-methylpyridin)yl]-3-butene-1-amine for which X is C-$OCH_3$, n is 2, A" and Z"

each are methyl, and A, A' and Z' each are hydrogen. Another representative compound is (E)-N-methyl-4-[3-(6-methylpyridin)yl]-3-butene-1-amine for which X is C—H, n is 2, A" and Z" each are methyl, and A, A' and Z' each are hydrogen. Another representative compound is (E)-4-[3-(6-methylpyridin)yl]-3-butene-1-amine for which X is C—H, n is 2, A" is methyl, and A, A', Z' and Z" each are hydrogen. Another representative compound is (E)-N-methyl-5-[3-pyridinyl]-4-pentene-1-amine for which X is C—H, n is 3, Z" is methyl, and A, A', A" and Z' are each hydrogen. Another representative compound is (E)-N-(2-propyl)-4-[3-pyridinyl]-3-butene-1-amine for which X is C—H, n is 2, Z" is isopropyl, and A, A', A" and Z' are each hydrogen.

The manner in which aryl substituted aliphatic amine compounds of the present invention are synthetically produced can vary. Preparation of various aryl substituted aliphatic amine compounds can be carried out using the types of techniques disclosed by Rondahi, *Acta Pharm. Suec.*, Vol. 13, pp. 229–234 (1976). Certain metanicotine-type compounds that possess a saturated side chain rather than an olefinic side chain can be prepared by hydrogenation of the corresponding metanicotine-type compounds or the corresponding acetylenic precursors. For example, dihydrometanicotine can be prepared by hydrogenation of (E)-metanicotine as described by Kamimura et al., *Agr. Biol. Chem.*, Vol. 27, No. 10, pp. 684–688 (1963).

The manner in which aryl substituted acetylenic amine compounds of the present invention are synthetically produced can vary. For example, an aryl substituted acetylenic amine compound, such N-methyl-4-(3-pyridinyl)-3-butyne-1-amine, can be prepared using a number of synthetic steps: (i) conversion of 3-pyridinecarboxaldehyde to a 1,1-dihalo-2-(3-pyridinyl)-ethylene using a carbon tetrahalide and triphenylphosphine, (ii) side chain elaboration of this intermediate by reaction with butyl lithium and ethylene oxide, affording 4-(3-pyridinyl)-3-butyn-1-ol, (iii) conversion of this intermediate to its methanesulfonate ester, and (iv) mesylate displacement with methyl amine, affording N-methyl-4-(3-pyridinyl)-3-butyne-1-amine.

The manner in which aryl substituted olefinic amine compounds of the present invention are synthetically produced can vary. (E)-metanicotine can be prepared using the techniques set forth by Löffler et al., *Chem. Ber.*, Vol. 42, pp. 3431–3438 (1909) and Laforge, *J.A.C.S.*, Vol. 50, p. 2477 (1928). Certain novel 6-substituted metanicotine-type compounds can be prepared from the corresponding 6-substituted nicotine-type compounds using the general methods of Acheson et al., *J. Chem. Soc., Perkin Trans.* 1, Vol. 2, pp. 579–585 (1980). The requisite precursors for such compounds, 6-substituted nicotine-type compounds, can be synthesized from 6-substituted nicotinic acid esters using the general methods disclosed by Rondahi, *Acta Pharm. Suec.*, Vol. 14, pp 113–118 (1977). Preparation of certain 5-substituted metanicotine-type compounds can be accomplished from the corresponding 5-substituted nicotine-type compounds using the general method taught by Acheson et al., *J. Chem. Soc., Perkin Trans.* 1, Vol. 2, pp. 579–585 (1980). The 5-halo nicotine-type compounds (e.g., fluoro and bromo nicotine-type compounds) and the 5-amino nicotine-type compounds can be prepared using the general procedures disclosed by Rondahl, *Act. Pharm. Suec.*, Vol. 14, pp. 113–118 (1977). The 5-trifluoromethyl nicotine-type compounds can be prepared using the techniques and materials set forth in Ashimori et al., *Chem. Pharm. Bull.*, Vol. 38(9), pp. 2446–2458 (1990) and Rondahl, *Acta Pharm. Suec.*, Vol. 14, pp.113–118 (1977). Furthermore, preparation of certain rectanicotine-type compounds can be accomplished using a palladium catalyzed coupling reaction of an aromatic halide and a terminal olefin containing a protected amine substituent, removal of the protective group to obtain a primary amine, and optional alkylation to provide a secondary or tertiary amine. In particular, certain metanicotine-type compounds can be prepared by subjecting a 3-halo substituted, 5-substituted pyridine compound or a 5-halo substituted pyrimidine compound to a palladium catalyzed coupling reaction using an olefin possessing a protected amine functionality (e.g., such an olefin provided by the reaction of a phthalimide salt with 3-halo-1-propene, 4-halo-1-butene, 5-halo-1-pentene or 6-halo-1-hexene). See, Frank et al., *J. Org. Chem.*, Vol. 43(15), pp. 2947–2949 (1978) and Malek et al., *J. Org. Chem.*, Vol. 47, pp. 5395–5397 (1982). Alternatively, certain metanicotine-type compounds can be prepared by coupling an N-protected, modified amino acid residue, such as 4-(N-methyl-N-tert-butyloxycarbonyl)aminobutyric acid methyl ester with an aryl lithium compound, as can be derived from a suitable aryl halide and butyl lithium. The resulting N-protected aryl ketone is then chemically reduced to the corresponding alcohol, converted to the alkyl halide, and subsequently dehydrohalogenated to introduce the olefin functionality. Removal of the N-protecting group affords the desired metanicotine-type compound. There are a number of different methods for providing (Z)-metanicotine-type compounds. In one method, (Z)-metanicotine-type compounds can be synthesized from nicotine-type compounds as a mixture of E and Z isomers; and the (Z)-metanicotine-type compounds can then be separated by chromatography using the types of techniques disclosed by Sprouse et al., Abstracts of Papers, p. 32, Coresta/TCRC Joint Conference (1972). In another method, (Z)-metanicotine can be prepared by the controlled hydrogenation of the corresponding acetylenic compound (e.g., N-methyl-4-(3-pyridinyl)-3-butyne-1-amine). For example, certain 5-substituted (Z)-metanicotine-type compounds and certain 6-substituted (Z)-metanicotine-type compounds can be prepared from 5-substituted-3-pyridinecarboxaldehydes and 6-substituted-3-pyridinecarboxaldehydes, respectively.

A representative compound, (E)-N-methyl-4-[3-(5-bromopyridin)yl]-3-butene-1-amine, can be synthesized using the following representative procedure. 5-Bromonicotine (0.018 mole) in 10 ml of methylene chloride dried over phosphorous pentaoxide has a solution of ethyl chloroformate (0.018 mole) in 10 mL of similarly dried methylene chloride added dropwise over 10 to 15 minutes. The resulting mixture then is refluxed under nitrogen atmosphere for about 3 hours. Then, the methylene chloride is removed using a rotary evaporator, and the remaining material is distilled under reduced pressure to yield a N-ethylcarbamate derivative of 5-bromometanicotine product as a thick liquid which has a boiling point of 182° C. at 0.04 mm Hg. This product (0.08 mole) is then refluxed for several hours in 15 ml of concentrated aqueous hydrochloric acid. The resulting reaction mixture was cooled and basified to pH 8–9 using concentrated aqueous sodium hydroxide while the mixture is maintained at a temperature of about 0° C. The resulting product is extracted four times with 20 ml quantities of chloroform, and the combined collected fractions are dried over anhydrous sodium sulfate. Then, the chloroform is removed using a rotary evaporator, and the remaining material is distilled under reduced pressure to yield the (E)-N-methyl-4-[3-(5-bromopyridin)yl]-3-butene-1-amine product as a colorless liquid which has a boiling point of 115° C. at 0.04 mm Hg. That product can be converted to a fumarate salt, which has a melting point of 148°–150° C.

A representative compound, (E)-N-methyl-5-[3-pyridinyl]-4-pentene-1-amine, can be synthesized using the following representative procedure. A solution of N-methyl anabasine (0.011 mole) in 100 mL methylene chloride is added dropwise into a slight molar excess of ethyl chlorofomate in 100 mL methylene chloride under nitrogen atmosphere in a flask equipped with a condenser. Then, the mixture is refluxed for about 3 hours. Then, the methylene chloride is removed using a rotary evaporator, and the remaining material is distilled using a short-path distillation apparatus to yield N-ethylcarbamate of trans-homomcticotine product as a colorless liquid which has a boiling point of 170°–172° C. at 1 mm Hg. This product (0.012 mole) is dissolved in 50 mL concentrated aqueous hydrochloric acid, and the resulting mixture is refluxed overnight. The reaction mixture then is cooled. The resulting product is extracted four times with 20 mL quantities of chloroform, and the combined collected fractions are dried over anhydrous sodium sulfate. Then, the chloroform is removed using a rotary evaporator, and the remaining material is distilled under reduced pressure to yield the (E)-N-methyl-5-[3-pyridinyl]-4-pentene-1-amine product as a colorless liquid which has a boiling point of 81°–82° C. at 4 mm Hg. That product can be converted to a fumarate salt, which has a reciting point of 139°–140° C.

A representative compound, (E)-N-(2-propyl)-4-[3-pyridynyl]-3-butene-1-amine, can be synthesized using the following representative procedure. (E)-4-[3-pyridynyl]-3-butene-1-amine (0.5 millimole) is prepared according to the procedure of Heck, *J. Org. Chem.*, Vol. 43, pp. 2947 (1978), combined with 2-iodepropane (0.525 millimole) and potassium carbonate (1 millimole), and refluxed in 30 mL tetrahydrofuran for 36 hours. Then, the tetrahydrofuran is removed using a rotary evaporator and 5 mL ethyl ether is added to the remaining residue. Filtration followed by concentration on a rotary evaporator yields a brown oil which can be purified by column chromatography followed by distillation under reduced pressure (138°–140° C. at 0.25 mm Hg) to yield the (E)-N-(2-propyl)-4-[3-pyridynyl]-3-butene-1-amine product.

A representative compound, (E)-N-methyl-4-[3-(5-aminopyridin)yl]-3-butene-1-amine, can be synthesized using the following representative procedure. 5-Amino nicotine (1 millimole) is prepared according to the procedure of Rondahl,. *Acta, Pharm. Suec.*, Vol. 14, pp. 113 (1977), combined with phthalic anhydride (1 millimole), and refluxed in 3 mL toluene for 16 hours using a Dean-Stark trap. The reaction mixture is cooled to ambient temperature and the toluene is removed using a rotary evaporator. To the remaining residue is added 2 mL methylene chloride, followed by dropwise addition of ethyl chloroformate (1.1 millimole) under nitrogen atmosphere. The resulting mixture is refluxed for 8 hours, cooled to ambient temperature, and concentrated on a rotary evaporator. The resulting viscous oil is heated to 160° C. under vacuum for one hour, and then cooled to ambient temperature. Then, 10 mL of a 10 percent aqueous solution of sodium bicarbonate is added to the reaction mixture. That mixture then is extracted three times with 15 mL portions of chloroform. The combined portions then are dried over anhydrous potassium carbonate. Filtration followed by evaporation of chloroform yields a pale brown oil. This oil is dissolved in 1 mL tetrahydrofuran followed by 2 mL of a solution 2 parts methyl amine in 3 parts water. This mixture is stirred for 10 hours. Then, tetrahydrofuran and excess methyl amine are removed using a rotary evaporator. Concentrated aqueous hydrochloric acid (5 mL) is added to the reaction mixture followed by reflux for several hours. The acidic solution, after cooling to ambient temperature, is extracted three times with 10 mL portions of ethyl acetate. Then, the acidic solution is basified using potassium carbonate and then sodium hydroxide. The basic solution then is extracted four times with 10 mL portions of n-butyl alcohol. The combined extracts are dried over anhydrous magnesium sulfate. Filtration, followed by concentration on a rotary evaporator yields the (E)-N-methyl-4-[3-(5-aminopyridin)yl]-3-butone-1-amine product as a dark brown oil. The product can be purified by column chromatography using a chloroform:methanol:triethylamine (60:20:20) solvent system as an eluent.

The present invention relates to a method for providing prevention of a CNS disorder to a subject susceptible to such a disorder, and for providing treatment to a subject suffering from a CNS disorder. In particular the method comprises administering to a patient an amount of a compound effective for providing some degree of prevention of the progression of the CNS disorder (i.e., provide protective effects), amelioration of the symptoms of the CNS disorder, and amelioration of the reoccurrence of the CNS disorder. The method involves administering an effective amount of a compound selected from the general formulae which are set forth hereinbefore. The present invention relates to a pharmaceutical composition incorporating a compound selected from the general formulae which are set forth hereinbefore. The compounds normally are not optically active. However, certain compounds can possess substituent groups of a character so that those compounds possess optical activity. Optically active compounds can be employed as racemic mixtures or as enantiomers. The compounds can be employed in a free base form or in a salt form (e.g., as pharmaceutically acceptable salts, such as chloride, perchlorate, ascorbate, sulfate, tartrate, fumarate, citrate, malate, lactate or aspartate salts). CNS disorders which can be treated in accordance with the present invention include presenile dementia (early, onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

The pharmaceutical composition also can include various other components as additives or adjuncts. Exemplary pharmaceutically acceptable components or adjuncts which are employed in relevant circumstances include antioxidants, free radical scavenging agents, peptides, growth factors, antibiotics, bactcriostatic agents, immunosuppressives, buffering agents, anti-inflammatory agents, anti-pyretics, time release binders, anaesthetics, steroids and corticosteroids. Such components can provide additional therapeutic benefit, act to affect the therapeutic action of the pharmaceutical composition, or act towards preventing any potential side effects which maybe posed as a result of administration of the pharmaceutical composition. In certain circumstances a compound of the present invention can be employed as part of a pharmaceutical composition with other compounds intended to prevent or treat a particular CNS disorder.

The manner in which the compounds are administered can vary. The compounds can be administered by inhalation (e.g., in the form of an aerosol either nasally or using delivery articles of the the set forth in U.S. Pat. No. 4,922,901 to Brooks et al.); topically, (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); or transdermally (e.g., using a transdermal patch). Although it is possible to administer the compounds in the form of a bulk active chemical it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Ciba-Geigy Corporation and Alza Corporation. The administration of the pharmaceutical compositions of the present invention can be intermittent, or at a gradual, continuous, constant or controlled rate to a warm-blooded animal, such as a human being. In addition, the time of day and the number of times per day that the pharmaceutical formulation is administered can vary. Administration preferably is such that the active ingredients of the pharmaceutical formulation interact with receptor sites within the body of the subject that effect the functioning of the CNS.

The dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, an effective amount of compound is an amount sufficient to pass across the blood-brain barrier of the subject, to bind to relevant receptor sites in the brain of the subject, and to elicit neuropharmacological effects (e.g., elicit neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the reoccurrence of the symptoms of the disorder.

The effective dose can vary depending upon factors such as the condition of the patient the severity of the symptoms of the disorder, and the manner in which the pharmaceutical composition is administered. For human patients the effective dose of typical compounds generally requires administering the compound in an amount of at least about 1, often at least about 10, and frequently at least about 25 mg/24 hr./patient. For human patients, the effective dose of typical compounds requires administering the compound which generally does not exceed about 500, often does not exceed about 400, and frequently does not exceed about 300 mg/24 hr./patient. In addition administration of the effective dose is such that the concentration of the compound within the plasma of the patient normally does not exceed 500 ng/ml, and frequently does not exceed 100 ng/ml.

The compounds useful according to the method of the present invention have the ability to pass across the blood-brain barrier of the patient. As such, such compounds have the ability to enter the central nervous system of the patient. The log P values of typical compounds useful in carrying out the present invention generally are greater than −0.5, often are greater than about 0, and frequently are greater than about 0.5. The log P values of such typical compounds generally are less than about 3.0, often are less than about 2.5, and frequently are less than about 2.0. Log P values provide a measure of the ability of a compound to pass across a diffusion barrier such as a biological membrane. See, Hansch, et al., *J. Med. Chem.*, Vol. 11, p. 1 (1968).

The compounds useful according to the method of the present invention have the ability to bind to, and in most circumstances, cause activation of, nicotinic cholinergic receptors of the brain of the patient. As such, such compounds have the ability to express nicotinic pharmacology, and in particular, to act as nicotinic agonists. The receptor binding constants of typical compounds useful in carrying out the present invention generally exceed about 1 nM, often exceed about 200 nM; and frequently exceed about 500 nM. The receptor binding constants of such typical compounds generally are less than about 10 uM, often are less than about 7 uM, and frequently are less than about 2 uM. Receptor binding constants provide a measure of the ability of the compound to bind to half of the relevant receptor sites of certain brain cells of the patient. See, Cheng, et al., *Biochem. Pharmacol.*, Vol. 22, pp. 3099–3108 (1973).

The compounds useful according to the method of the present invention have the ability to demonstrate a nicotinic function by effectively eliciting neurotransmitter secretion from nerve ending preparations (i.e., synaptosomes). As such, such compounds have the ability to cause relevant neurons to release or secrete acetylcholine, dopamine, and other neurotransmitters. Generally, typical compounds useful in carrying out the present invention provide for the secretion of dopamine in amounts of at least about 25 percent, often at least about 50 percent, and frequently at least about 75 percent, of that elicited by an equal molar amount of S(−) nicotine. Certain compounds of the present invention can provide secretion of dopamine in an amount which can exceed that elicited by an equal molar amount of (S)-(−)-nicotine.

The compounds of the present invention, when employed in effective amounts in accordance with the method of the present invention, lack the ability to elicit activation of nicotinic receptors of human muscle to any significant degree. In that regard, the compounds of the present invention demonstrate poor ability to cause isotopic rubidium ion flux through nicotinic receptors in cell preparations derived from muscle preparations. Thus, such compounds exhibit receptor activation constants or EC50 values (i.e., which provide a measure of the concentration of compound needed to activate half of the relevant receptor sites of the skeletal muscle of a patient) which are relatively high. Generally, typical compounds useful in carrying the present invention activate isotopic rubidium ion flux by less than 15 percent, often by less than 10 percent, and frequently by less than 5 percent, of that elicited by an equal molar amount of (S)-(−)-nicotine.

The compounds of the present invention, when employed in effective amounts in accordance with the method of the present invention, are selective to certain relevant nicotinic receptors, but do not cause significant activation of receptors associated with undesirable side effects. By this is meant that a particular dose of compound resulting in prevention and/or treatment of a CNS disorder is essentially ineffective in eliciting activation of certain ganglionic-type nicotinic receptors. This selectively of the compounds of the present invention against those receptors responsible for cardiovascular side effects is demonstrated by a lack of the ability of those compounds to activate nicotinic function of adrenal chromaffin tissue. As such, such compounds have poor ability to cause isotopic rubidium ion flux through nicotinic receptors in cell preparations derived from the adrenal gland. Generally, typical compounds useful in carrying the present invention activate isotopic rubidium ion flux by less than 15 percent, often by less than 10 percent, and frequently by less than 5 percent, of that elicited by an equal molar amount of (S)-(−)-nicotine.

Compounds of the present invention, when employed in effective amounts in accordance with the method of the present invention, are effective towards providing some degree of prevention of the progression of CNS disorders amelioration of the symptoms of CNS disorders and amelioration to some degree of the reoccurrence of CNS disorders. However, such effective amounts of those compounds are not sufficient to elicit any appreciable side effects, as demonstrated by increased effects relating to the cardiovascular system, and effects to skeletal muscle. As such, administration of compounds of the present invention provides a therapeutic window in which treatment of certain CNS disorders is provided, and side effects are avoided. That is, an effective dose of a compound of the present invention is sufficient to provide the desired effects upon the CNS, but is insufficient (i.e., is not at a high enough level) to provide undesirable side effects. Preferably, effective administration of a compound of the present invention resulting in treatment of CNS disorders occurs upon administration of less than 1/5, and often less than 1/10, that amount sufficient to cause any side effects to a significant degree.

The following example is provided in order to further illustrate various embodiments of the invention but should not be construed as limiting the scope thereof. Unless otherwise noted, all parts and percentages are by weight.

EXAMPLE

Sample No. 1 is (E)-4-(5-pyrimidinyl)-3-butene-1-amine monofumarate (compound III monofumarate), which was prepared essentially in accordance with the following techniques.

N-3-Butene-1-phthalimide (I):

This compound was prepared essentially in accordance with the techniques described in Heck, et al., *J. Org. Chem.*, Vol. 43. pp. 2947–2949 (1978).

(E)-N-[4-(5-Pyrimidinyl)-3-butene-1-]phthalimide (II):

Under a nitrogen atmosphere, a mixture of I (28.20 g, 140 mmol), 5-bromopyrimidine (21.63 g, 136 mmol), palladium(II) acetate (306 mg, 1.4 mmol), tri-o-tolylphosphine (828 mg. 2.7 mmol), and triethylamine (27.54 g, 272 mmol) was stirred and heated at ~110° C. for 27 h. The precipitated brown solids were slurried m water filtered, and dissolved in hot N,N-dimethylformamide (DMF) (75 mL). Charcoal (Darco® G-60, 1 g) was added and the mixture filtered through Celite® (1.8 g), washing the filter cake with hot DMF (10 mL). The filtrate was diluted with an equal volume of water and cooled at 5° C. for 15 h. The solids were filtered, washed with water (2×25 mL) and dried, producing a beige, crystalline powder (28.55 g, 75.1%). Further purification, involving two recrystallizations from DMF-water (1:1), followed by two recrystallizations from toluene afforded compound II as a light beige, crystalline powder (18.94 g, 49.8%), mp 177°–178.5° C.

IR (KBr): 3445 (w), 3014 (w), 2951 (w), 1768 (m, C=O), 1703 (s, C=O), 1650 (w, C=C), 1558 (m), 1433 (s), 1402 (s), 1367 (s), 1330 (m), 1057 (m), 964 (m, trans C=C), 879 (m), 721 (s, 1,2-disubst. benzene), 717 (w, 5-pyrimidinyl), 633 (w, 5-pynmidinyl) cm$^{-1}$.

$^1$H NMR (CDCl$_3$): δ9.01 (s, 1H), 8.60 (s, 2H), 7.85 (m, 2H), 7.70 (m, 2H), 6.35 (m, 2H), 3.85 (m, 2H), 2.63 (m, 2H).

$^{13}$C NMR (CDCl$_3$): δ168.26, 157.21, 154.09, 134.07, 131.97, 131.37, 130.69, 125.60, 123.33, 37.11, 32.49.

EI-MS: m/z (relative intensity) 279 (M$^+$, 5%), 160 (100%), 131 (43%), 119 (45%), 104(17%), 77 (31%), 65(13%),51 (11%).

HRMS: Calcd. for C$_{16}$H$_{13}$N$_3$O$_2$ (M$^+$): m/z 279.0992. Found: 279.1008.

Anal. Calcd. for C$_{16}$H$_{13}$N$_3$O$_2$: C, 68.81; H, 4.69; N, 15.05. Found: C, 68.68; H, 4.82; N, 14.94.

(E)-4-(5-Pyrimidinyl)-3-butene-1-amine (III):

Hydrazine hydrate (2.69 g, 53.7 mmol, 99%) was added to a mixture of II (6.00 g, 21.5 mmol) and methanol (100 mL), and the mixture was stirred at ambient temperature for 27 h. The white suspension was diluted with 1M NaOH solution (400 mL) and extracted with chloroform (5×100 mL). The chloroform extracts were combined, dried (Na$_2$SO$_4$), filtered, and concentrated by rotary evaporation. The residue was vacuum dried 5 h at 55° C. to give (E)-4-(5-pyrimidinyl)-3-butene-1-amine (III) as a light yellow oil (2.95 g, 92.2%), which was used without further purification.

IR (film): 3345 (br, N—H), 1655 (m, C=C), 1560 (s), 1490 (s), 1440 (s), 1415 (s), 1390 (m), 1317 (s), 1190 (m), 968 (m, trans C=C), 721 (s, 5-pyrimidinyl), 636 (m, 5-pyrimidinyl) cm$^{-1}$.

$^1$H NMR (CDCl$_3$): δ9.13 (s, 1H), 8.68 (s, 2H), 6.38 (m, 2H), 2.84 (t, 2H, J=7 Hz), 2.40 (m, 2H), 1.26 (br s, 2H).

$^{13}$C NMR (CDCl$_3$): δ157.04, 153.96, 133.16, 130.92, 124.82, 41.36, 37.44.

EI-MS: m/z (relative intensity) 148 (M$^+$−1, 0.1%), 132 (1%), 120 (100%), 93 (31%), 66 (40%), 51 (11%), 44 (14%).

The monofumarate of III was prepared by adding a warm solution of fumaric acid (156 mg, 1.34 mmol) in ethanol (5 mL) to a warm solution of III (100 mg, 0.67 mmol) in ethanol (3 mL). The mixture was concentrated by rotary evaporation, and the slightly yellow solids were recrystallized from ethanol-ether (1:1). The solids were filtered, washed with ethanol, ether, and vacuum dried at 50° C. for 24 h, affording the monofumarate as a white, crystalline powder (63.8 mg, 35.9%), mp 160°–161.5° C.

IR (KBr): 3300–2300 (br, s, amine-carboxylate), 1705 (s, C=O), 1664 (s), 1606 (s, C=C), 1556 (s), 1409 (s, fumarate), 1254 (m), 1186 (m), 981 (m, trans C=C), 852 (m), 796 (m), 723 (w, 5-pyrimidinyl), 648 (m, fumarate), 631 (m, 5-pyrimidinyl) cm$^{-1}$.

$^1$H NMR (D$_2$O): δ9.00 (s, 1H), 8.84 (s, 2H), 6.69 (s, 2H), 6.63 (d, 1H, J=16.4 Hz), 6.52 and 6.46, (dt, 1H, J=16.1, 6.8 Hz), 3.20 (m, 2H), 2.72 (m, 2H).

$^{13}$C NMR (D$_2$O): δ171.45, 154.10, 134.63, 131.04, 130.23, 126.05, 38.40, 30.33.

Anal. Calcd. for C$_8$H$_{11}$N$_3$·C$_4$H$_4$O$_4$: C, 54.33; H, 5.70; N, 15.84. Found: C, 54.24; H, 5.75; N, 15.65.

Sample No. 2 is (E)-N-methyl-4-(5-pyrimidinyl)-3-butene-1-amine (compound VI), which was prepared essentially in accordance with the following techniques.

(E)-N-tert-Butyloxycarbonyl-4-(5-pyrimidinyl)-3-butene-1-amine (IV):

A solution of di-tert-butyl dicarbonate (2.66 g, 12.2 mmol) in methylene chloride (10 mL) was added dropwise over 5 min to a stirring solution of (E)-4-(5-pyrimidinyl)-3-butene-1-amine (III) (1.70 g, 11.4 mmol) in methylene chloride at 0° C. The yellow solution was stirred at 0° C. for 15 min and at ambient temperature for 22 h. Concentration by rotary evaporation, followed by vacuum drying at 30° C. for 15 h afforded a yellow oil. The oil was chromatographed on silica gel (165 g), eluting first with ethyl acetate to remove impurities. Elution with chloroform-methanol (2:1) afforded the product which was re-chromatographed eluting with ethyl acetate. Selected fractions were combined in chloroform and concentrated by rotary evaporation. The residue was vacuum dried at 35° C. for 48 h to give compound IV as a light yellow oil (2.56 g, 90.1%), which crystallized upon cooling, affording a light yellow, crystalline solid, mp 54°–55.5° C.

IR (KBr): 3030 (w), 2990 (w), 2980 (w), 2965 (w), 2935 (w), 3298 (s, amide N—H), 1712 (s, carbamate C═O), 1657 (w, C═C), 1560 (s), 1535 (s, amide N—H), 1433 (s), 1414 (s), 1367 (s, tert-butyl), 1275 (s, amide N—H), 1246 (s, ester C—O), 1174 (s, ester C—O), 1149 (s), 1111 (m), 987 (m), 966 (m trans C═C), 723 (w, 5-pyrimidinyl), 636 (m, 5-pyrimidinyl) cm$^{-1}$.

$^1$H NMR (CDCl$_3$): δ9.05 (s, 1H), 8.70 (s, 2H), 6.37 (m, 2H), 4.59 (br s, 1H), 3.30 (m, 2H), 2.43 (m, 2H), 1.46 (s, 9H).

$^{13}$C NMR (CDCl$_3$): δ157.34, 156.83, 155.84, 154.18, 153.79, 132.24, 130.75, 125.15, 79.42, 39.64, 34.05, 28.56, 28.20.

EI-MS: m/z (relative intensity) 249 (M$^+$, 0.1%), 193 (15%), 176 (24%), 132 (16%), 120 (79%), 119 (85%), 93 (19%), 65 (24%), 57 (100%).

Anal. Calcd. for C$_{13}$H$_{19}$N$_3$O$_2$: C, 62.62; H, 7.68; N, 16.86. Found: C, 62.61; H, 7.62; N, 16.78.

(E)-N-Methyl-N-tert-Butyloxycarbonyl-4-(5-pyrimidinyl)-3-butene-1-amine (V):

Under a nitrogen atmosphere sodium hydride (0.78 g, 19.5 mmol, 60% dispersion in oil) was added to a stirring solution of IV (0.50 g, 2.0 mmol), 1,2-dimethoxyethane (20 mL), DMF (25 mL), and a trace of diisopropylamine. The mixture was stirred at ambient temperature for 45 min, and a solution of iodomethane (2.59 g, 18.3 mmol) in 1,2-dimethoxyethane (5 mL) was added. The mixture was stirred at ambient temperature for 3 days, cooled, and water (25 mL) was added dropwise. The mixture was diluted with water (200 mL) and extracted with chloroform (7×50 mL). All chloroform extracts were combined, dried (Na$_2$SO$_4$), filtered, and concentrated by rotary evaporation. The residue was dried under high vacuum at ambient temperature to give a red-brown oil. The oil was chromatographed on silica gel (50 g), eluting with ethyl acetate. Selected fractions were combined, concentrated by rotary evaporation, and dried under high vacuum at ambient temperature to give compound V as a light yellow oil (0.40 g, 76.1%).

IR (film): 3650–3200 (br, w), 2980 (m), 2940 (m), 1697 (s, carbamate C═O), 1556 (s), 1484 (s), 1452 (s), 1420 (s, N—CH$_3$), 1411 (s, tert-butyl), 1394 (s, tert-butyl), 1369 (s), 1304 (m), 1249 (m, ester C—O), 1218 (s), 1163 (s, ester C—O), 1136 (s), 972 (m, trans C═C), 883 (m), 774 (m), 721 (m, 5-pyrimidinyl), 631 (m, 5-pyrimidinyl) cm$^{-1}$.

$^1$H NMR (CDCl$_3$): δ9.01 (s, 1H), 8.63 (s, 2H), 6.31 (m, 2H), 3.32 (m, 2H), 2.82 (s, 3H), 2.44 (m, 2H), 1.39 (s, 9H).

$^{13}$C NMR (CDCl$_3$): δ157.06, 155.70, 153.95, 132.49, 130.94, 124.73, 79.51, 34.38, 28.45.

EI-MS: m/z (relative intensity) 263 (M$^+$, 0.3%), 207 (5%), 190 (7%), 144 (24%), 133 (9%), 120 (39%), 93 (13%), 88 (15%), 65 (11%), 57 (100%), 44 (89%

HRMS: Calcd. for C$_{14}$H$_{21}$N$_3$O$_2$ (M$^+$): m/z 263.1634. Found: 263.1643.

(E)-N-Methyl-4-(5-pyrimidinyl)-3-butene-1amine (VI):

Under a nitrogen atmosphere, iodotrimethylsilane (0.50 g, 2.5 mmol) was added dropwise, at ambient temperature, to a stirring solution of V (0.33 g, 1.2 mmol) in chloroform (20 mL). The red-brown mixture was stirred 30 min and methanol (20 mL) was added. The mixture was stirred 1 h and concentrated by rotary evaporation. The residue was basified with 1M NaOH solution (25 mL) and extracted with chloroform (7×25 mL). The chloroform extracts were combined dried (Na$_2$SO$_4$) and concentrated by rotary evaporation affording a brown oil. The oil was chromatographed on silica gel (35 g), eluting with methanol-ammonium hydroxide (10:1). Selected fractions were combined, vacuum dried at 45° C. for 3 h. affording (E)-N-methyl-N-4-(5-pyrimidinyl)-3-butene-1-amine (VI) as a brownish-red low oil (0.12 g, 59.6%).

IR (film): 3148 (br, s, N—H), 1653 (s, C═C), 1560 (s), 1473 (m), 1435 (s), 1414 (s, N—CH$_3$), 970 (m, trans C═C), 721 (s, 5-pyrimidinyl), 636 (s, 5-pyrimidinyl) cm$^{-1}$.

$^1$H NMR (CDCl$_3$): δ9.02 (s, 1H), 8.68 (s, 2H), 6.37 (m, 2H), 2.76 (t, 2H, J=6.8 Hz), 2.46 (m, 5H, including a N—CH$_3$ singlet), 1.65 (br s, 1H).

$^{13}$C NMR (CDCl$_3$): δ157.09, 154.01, 132.99, 130.90, 124.81, 50.76, 36.06, 33.35.

EI-MS: m/z (relative intensity) 146 (0.3%), 132 (0.4%), 120 (22%), 93 (4%), 65 (4%) 44 (100%).

HRMS: Calcd. for C$_7$H$_8$N$_2$ (M$^+$–44): m/z 120.0676. Found: 120.0687.

Sample No. 3 is (E)-4-[3-(5-methoxypyridin)yl]-3-butene-1-amine monoformarate (compound IX monofumarate), which was prepared essentially in accordance with the following techniques.

3-Bromo-5-methoxypridine (VII)

This compound was prepared essentially in accordance with the techniques described in Comins et al., *J. Org. Chem.*, Vol. 55, pp. 69–73 (1990).

(E)-N-4-[3-(5-methoxypyridin)yl]-3-butene-1-phthalimide (VIII):

Under a nitrogen atmosphere, a mixture of N-3-butene-1-phthalimide (I) (5.51 g, 27.4 mmol), 3-bromo-5-methoxypyridine (VII) (5.00 g, 26.6 mmol), palladium(II) acetate (59.7 mg, 0.27 mmol), tri-o-tolylphosphine (162 mg, 0.53 mmol), and triethylamine (5.38 g, 53.2 mmol) was stirred and heated at ~100° C. for 21 h. The precipitated brown solids were slurried in water, filtered, and dissolved in hot DMF (30 mL). The mixture was filtered through Celite® (1 g), washing the filter cake with hot DMF (10 mL). The filtrate was diluted with an equal volume of water and cooled at 5° C. for 15 h. The solids were filtered, washed with water (2×10 mL), cold ethanol (10 mL), and dried, producing a beige, crystalline powder (7.79 g, 95.0%). Further purification, involving two recrystallizations from DMF-water (1:1) afforded compound VIII as a light beige, crystalline powder (5.36 g, 65.4%), mp 148°–151° C. An analytical sample was recrystallized from toluene, affording a light beige, crystalline powder, mp 148°–151.5° C.

IR (KBr): 3440 (w), 3040 (m), 2960 (s), 2940 (s), 2825 (w), 1766 (m, C═O), 1700 (s, C═O), 1654 (m, C═C), 1580 (m, pyridinyl), 1455 (s), 1420 (s), 1320 (m), 1190 (m), 1000 (s), 973 (s, trans C═C), 867 (s, 3,5-disubst. pyridine), 723 (s, 1,2-disubst. benzene), 703 (s, 3.5-disubst. pyridine) cm$^{-1}$.

$^1$H NMR (CDCl$_3$): δ8.14 (s, 1H), 8.08 (s, 1H), 7.82 (m, 2H), 7.69 (m, 2H), 7.10 (dd, 1H, J=2.4, 2.0 Hz), 6.38 (d, 1H, J=16.1 Hz), 6.25 and 6.20 (dt, 1H, J=15.9, 6.8 Hz), 3.84 (t, 5H, including an O—CH$_3$ singlet, J=7.1 Hz), 2.62 (dq, 2H, J=7.1, 1.0 Hz).

$^{13}$C NMR (CDCl$_3$): δ168.27, 155.73, 140.72, 136.45, 133.96, 132.05, 129.00, 123.26, 116.80, 55.52, 37.34, 32.30.

EI-MS: m/z (relative intensity) 308 (M$^+$, 13%), 160 (100%), 148 (8%), 133 (10%), 105(8%), 77 (15%).

Anal. Calcd. for C$_{18}$H$_{16}$N$_2$O$_3$: C, 70.12: H, 5.23; N, 9.09. Found: C, 70.34; H, 5.29; N, 9.00.

(E)-4-[3-(5-methoxypyridin)yl]-3-butene-1-amine (IX):

Hydrazine hydrate (245 mg, 4.90 mmol, 99%) was added to a mixture of VIII (500 mg, 1.62 mmol) and methanol (20 mL), and the mixture was stirred at ambient temperature for 20 h. The gray suspension was diluted with 1M NaOH solution (190 mL) and extracted with chloroform (5×25 mL). The chloroform extracts were combined, dried ($Na_2SO_4$), filtered, and concentrated by rotary evaporation. The crude product (287 mg) was further purified by vacuum distillation, affording compound IX (183 mg, 62.3%) as a light yellow oil, bp 110° C. at 0.05 mm Hg.

IR (film): 3350 (br, s), 3035 (s), 2940 (s), 2840 (m), 1585 (s), 1460 (s), 1425 (s), 1320 (s), 1295 (s, ArO—$CH_3$), 1185 (m), 1160 (m), 1050 (m), 1020 (sh), 965 (s, trans C=C), 885 (m, 3,5-disubst. pyridine), 820 (w), 710 (m, 3,5-disubst. pyridine).

$^1$H NMR ($CDCl_3$): δ8.16 (d, 1H, J=2.0 Hz), 8.13 (d, 1H, J=2.9 Hz), 7.14 (dd, 1H, J=2.6. 2.0 Hz), 6.41 (d, 1H, J=15.9 Hz), 6.27 and 6.22 (dt, 1H, J=15.9, 7.1 Hz), 3.84 (s, 3H), 2.84 (t, 2H, J=6.6 Hz), 2.36 (dq, 2H, J=6.6, 1.0 Hz).

$^{13}$C NMR ($CDCl_3$): 155.79, 140.70, 136.24, 133.72, 130.79, 128.27, 116.91, 55.57, 37.29, 29.70.

EI-MS: m/z (relative intensity) 178 ($M^+$, 0.4%), 149 (88%), 148 (100%), 133 (12%), 105 (9%), 78 (10%).

The monofumarate of IX was prepared by adding a warm solution of fumaric acid (131 mg, 1.12 mmol) in 2-propanol (15 mL) to compound IX (166 mg, 0.93 mmol). After stirring 30 min, the solution was concentrated by rotary evaporation to a white powder. The crude product was recrystallized from 2-propanol, and the mixture was stored at ambient temperature for 15 h. The solids were filtered, washed with cold 2-propanol, ether, and vacuum dried at 50° C. for 6 h, affording the monofumarate as a white, crystalline powder (177 mg, 64.6%), mp 151°–153° C.

IR (KBr): 3300–2400 (br, s, amine-carboxylate), 1700 (s, C=O), 1630 (s, C=O), 1570 (sh), 1535 (m), 1460 (m), 1435 (m), 1290 (s, ArO—$CH_3$), 1158 (m), 1040 (m), 982 (s, trans C=C), 875 (m, 3,5-disubst. pyridine), 793 (m), 705 (m, 3,5-disubst. pyridine), 652 (m).

$^1$H NMR($D_2O$): δ8.31 (s, 1H), 8.25 (s, 1H), 7.85 (s, 1H), 6.68 (d, 1H, J=16.1 Hz), 6.57 (s, 2H), 6.53 and 6.48 (dt, 1H, J=15.9, 7.1 Hz), 3.98 (s, 3H), 3.21 (t, 2H, J=7.1 Hz), 2.68 (q, 2H, J=7.1 Hz).

$^{13}$C NMR ($D_2O$): δ172.93, 156.77, 136.17, 135.62, 134.90, 131.81, 130.25, 128.04, 122.44, 56.31, 38.54, 30.14.

Anal. Calcd. for $C_{10}H_{14}N_2O·C_4H_4O_4$: C, 57.14; H, 6.16; N, 9.52. Found: C, 56.91; H, 6.18; N, 9.51.

Sample No. 4 is N-Methyl-4-(3-pyridinyl)-3-butyne-1-amine which was prepared essentially in accordance with the following techniques.

1,1-Dibromo-2-(3-pyridinyl)-ethylene (X)

Tetrabromomethane (24.82 g, 0.747 mole) and triphenylphosphine (39.17 g, 0.149 mole) were stirred together in dry methylene chloride (100 mL) for 5 min. at 0° C. under a nitrogen atmosphere. To this mixture was added dropwise pyridine 3-carboxaldehyde (4 g, 0.0373 mole). The solution was then stirred for 45 min. at ambient temperature. The reaction mixture was extracted with aqueous 6N hydrochloric acid (3×25 mL), the aqueous layer basified with solid sodium bicarbonate to pH 8–9 and extracted with chloroform (4×25 mL). The combined organic liquours were dried over anhydrous sodium sulfate, filtered and concentrated on a rotary evaporator to give a dark colored syrup. The crude product was chromatographed on silica gel (70–230 mesh) with chloroform:methanol (95:5) as eluant, to afford a light yellow solid (5.0 g, 70%) which rapidly turned dark on standing.

$^1$H NMR ($CDCl_3$) δ8.65 (s, 1H), 8.58 (d, 1H), 8.00 (d, 1H), 7.45 (s, 1H), 7.22–7.36 (m, 1H).

Anal. calcd. for $C_7H_4NBr_2$: C, 31.94; H, 1.90; N, 5.32; Br, 60.84. Found: C, 32.11; H, 2.03: N, 5.50: Br, 60.99.

4:(3 -Pyridinyl)-3-butyne-1ol (XI)

To dry THF (10 mL) contained in a 50 mL round-bottomed flask fixed with a nitrogen gas balloon was added X (2.5 g, 0.01 mole). The flask was cooled to –78° C. in an acetone-dry ice bath, and n-butyl lithium in THF (22 mL of a 2.5 molar solution in THF) was added dropwise via a syring during constant stirring. After addition, the solution was stirred for 1 hour. The reaction mixture temperature was then adjusted to –60° C. and ethylene oxide (1 mL) was added in one portion, and the reaction was allowed to warm to ambient temperature with stirring. The resulting reaction mixture was quenched with water (10 mL) and extracted with chloroform (3×25 mL), the combined organic liquors dried over anhydrous sodium sulfate, filtered and concentrated on a rotary evaporator under reduced pressure. The resulting oil was chromatographed on silica gel to afford the product as a light brown liquid (590 mg, 40%).

$^1$H NMR ($CDCl_3$) δ8.71 (s, 1H), 8.49 (d, 1H), 7.68 (d, 1H) 7.29–7.36 (m, 1H), 3.92 (t, 2H), 2.80(m, 2H).

Anal. calcd. for $C_9H_9NO$: C, 73.46; H, 6.12; N, 9.52. Found: C, 73.61; H, 6.31; N, 9.66.

Methanesulfonate ester of 4-(3-Pyridinyl)-3-butyne-1-ol (XII)

In dry methylene chloride (2 mL) was dissolved XI (0.15 g, 1.0 mmole), and to this solution was added triethylamine (0.184 ml, 1.3 mmole). The reaction was stirred overnight under nitrogen atmosphere. The mixture was cooled to 4° C. and methane sulfonyl chloride (0.15 g, 1.3 mmole) was added. The reaction mixture was then poured over ice/water (10 mL) and the resulting mixture stirred for 5 min. To this mixture was added saturated aqueous sodium bicarbonate solution (5 mL) chilled to 4° C., and the mixture stirred for 30 min., then extracted with chloroform (4×10 mL). The combined organic fractions were dried over anhydrous sodium sulfate, filtered and the volume concentrated on a rotary evaporator. The product was further purified using gel chromatography, eluting with a chloroform: methanol mixture containing 1% triethylamine. Yield of XII is 0.218 g (about 97%).

$^1$H NMR ($CDCl_3$) δ8.59 (s, 1H, 7.62 (d, 1H, 7.18–7.22 (m, 1H), 4.31 (t, 2H), 3.00 (s, 3H), 2.80 (t, 2H).

N-Methyl-4-3-pyridinyl)-3-butyne-1amine (XIII)

An aqueous methylamine solution (5mL, 40%, 58.7 mmole) was mixed with XII (200 mg, 0.08 mmole) and stirred for 3 hr. in a scaled tube at 45° C. After the reaction was complete, water (10 mL) was added to the cooled reaction mixture, and the reaction mixture was extracted with chloroform (10×5 mL). The combined organic extracts were dried over anhydrous sodium sulfate, filtered and concentrated The residue obtained was chromatographed on a silica gel column using methanol:chloroform (1:9) and then with a chloroform: methanol mixture containing 1% triethylamine as eluent. About 70 mg of XIII was obtained as a slightly yellow syrup, which was distilled at 110°–112° C., 0.04 mm Hg. XIII was converted to its mono fumarate salt form, which exhibits a melting point of 103°–104° C.

Free base. $^1$H NMR ($CDCl_3$) δ8.61 (s, 1H), 8.48 (d, 1H), 7.62 (d, 1H), 7.20 (t, 1H), 2.82 (t, 2H), 2.61 (t, 2H), 2.33 (s, 3H), 1.4 (br s, 1H).

Fumarate salt. $^1$H NMR ($D_2O$) δ8.51 (s, 1H), 8.39 (d, 1H), 7.91 (d, 1H), 7.40 (m, 1H), 6.28 (s, 2H), 3.20 (t, 2H), 2.80 (t, 2H), 2.62 (s, 3H).

¹³C NMR (D₂O) δ164.5, 151.8, 148.0, 146.0, 138.8, 128.2, 124.5, 93.0, 82.3, 50.4, 36.2, 20.1.

Anal. calcd. for $C_{14}H_{16}N_2O_4$: C, 60.86; H, 5.70; N, 10.14. Found: C, 60.84; H, 5.72; N. 10.23.

Sample No. 5 is (Z)-metanicotine which was prepared essentially in accordance with the following techniques, (Z)-Metanicotine (XIV)

Into a hydrogenation bottle together with methanol (20 mL), glacial acetic acid (1 mL) and a catalytic amount of quinoline was placed XIII free base (200 mg, 1.25 mmole). Lindlar's catalyst (palladium/calcium carbonate poisoned with lead) (60 mg) was added and the mixture hydrogenated at 50 psig in a Parr reaction apparatus overnight at ambient temperature. The catalyst was filtered off, the resulting solution basified with aqueous sodium hydroxide (50% w/v) to a pH 8–9, and then extracted with chloroform (3×25 mL). The combined organic liquors were concentrated on a rotary evaporator, and the residue chromatographed on 60–230 mesh silica gel, using chloroform:methanol: triethylamine (90:10:1) as eluent, to afford XIV as a colorless oil at about 100% yield. XIV is converted to its difumarate salt, which has a reciting point of 117°–118° C.

Free-base, ¹H NMR (CDCl₃) δ8.56 (s, 1H), 8.42 (d, 1H), 7.60 (d, 1H), 7.22 (m, 1H), 6.81 (m, 1H), 6.51 (d, 1H), 2.79 (t, 2H), 2.52 (m, 2H), 2.41 (s, 3H).

Difumarate salt. ¹H NMR (D₂O) δ8.48 (br s, 2H), 8.10 (d, 1H), 7.75–7.63 (m, 1H), 6.52 (d, 1H), 6.40 (s, 1H), 5.85–5.78 (m, 1H), 3.00 (t, 2H), 2.51 (m, 5H).

Anal. calcd. for $C_{10}H_{14}N_2·2C_4H_4O_4$; C, 54.82; H, 5.58; N, 7.10. Found: C, 54.47; H, 5.68; N, 6.98.

Sample No. 6 is (E)-N-methyl-4-[3-(6-methylpyridin)yl]-3-butene-1-amine which was prepared essentially in accordance with the following techniques.

6-Methylmyosmine (XV)

Sodium hydride (60% in oil) (1.9 g, 0.079 mole) was placed in a 250 mL two-necked round bottom flask and washed with dry THF (50 mL). A further aliquot of dry THF (100 mL) was added followed by a solution of N-vinylpyrrolidone (4.7 g. 0.04 mole) in dry THF (30 mL), and the mixture stirred for 30 min. at ambient temperature. A solution of ethyl 6-methylnicotinate (5.0 g, 0.033 mole) in dry THF (20 mL) was then added dropwise over 10 min., during which time evolution of hydrogen occurred. The reaction was flushed with nitrogen, and the mixture refluxed for 6 hr. After cooling, aqueous hydrochloric acid (6N, 25 mL) was added and the THF removed by rotary evaporation under reduced pressure. A further volume of aqueous hydrochloric acid (6N, 20 mL) was added and the mixture refluxed overnight. On cooling, the mixture was basified with aqueous sodium hydroxide (50% w/v) to pH 8–9, and XV was extracted with chloroform (5×20 mL). The combined organic liquours were dried over anhydrous sodium sulfate, filtered and the solvent evaporated to afford XV, which was crystallized from methanol as a tan solid (4.45 g, 84%).

¹H NMR (CDCl₃) δ8.82 (s, 1H), 8.15 (d, 1H), 7.20 (d, 1H), 4.12 (t. 2H). 2.98 (t, 2H). 2.80 (s, 3H), 2.00 (m, 2H).

¹³C NMR(CDCl₃) δ172.5, 160.08, 148.1, 135.01, 122.7, 61.5, 34.8, 24.2, 22.2.

Anal. calcd. for $C_{10}H_{12}N_2$: C, 75.00, H, 7.50; N, 17.50. Found: C, 74.94; H, 7.51; N. 17.47.

(+/−)-6-Methylnomicotine (XVI)

Into a round bottom flask was placed XV (3.0 g, 0.018 mole), methanol (20 mL) and glacial acetic acid (4 mL). The mixture was cooled to −78° C. in a dry ice-acetone bath, and sodium borohydride (1.332 g, 0.36 mole) was added over 30 mm. After addition, the reaction mixture was allowed to warm to ambient temperature, and stirred for 1 hr. The methanol then was removed on a rotary evaporator under reduced pressure and the residue was basified with aqueous sodium hydroxide (50% w/v) to pH 8–9. The aqueous solution was extracted with chloroform (5×25 mL) and the combined organic liquors dried over anhydrous sodium sulfate, filtered and evaporated on a rotary evaporator to afford XVI as a dark brown liquid, which was distilled at 4 mm Hg to yield a clear, colorless liquid (b.p. is 113°–114° C. 4 mm Hg) (2.43 g, 80%).

¹H NMR (CDCl₃) δ8.42 (s, 1H), 7.60 (d, 1H), 7.10 (d, 1H), 4.15 (t, 1H), 3.12 (m, 1H), 3.00 (m, 1H), 2.30 (s, 3H), 2.20–2.00 (m, 2H), 2.00–1.98 (m, 2H), 1.78–1.60 (m, 1H).

HClO₄ salt ¹H NMR (D₂O) δ8.62 (s, 1H), 8.40 (d, 1H), 7.81 (d, 1H), 3.58 (t, 2H), 2.78 (s, 3H), 2.40–2.20 (m, 4H).

Anal. calcd. for $C_{10}H_{16}N_2Cl_2O_8$: C, 33.05; H, 4.40; N. 7.71; Cl. 19.55. Found: C, 33.16; H, 4.46; N, 7.64; Cl, 19.43.

(+/−)-6-Methylnicotine (XVII)

Into a round bottom flask was placed XVI (2.0 g), and formaldehyde (37% w/v in water, 20 mL) and foretic acid (95–97% w/v, 45 mL), both at 0° C. were added. The mixture then was refluxed under nitrogen for 8 hr. The cooled reaction mixture was basified with aqueous sodium hydroxide (50% w/v) to pH 8–9, and the solution extracted with chloroform (5×25 mL). The combined organic liquors were dried over anhydrous sodium sulfate, filtered and evaporated; and the resulting oil distilled under reduced pressure to afford XVII as a clear odorless oil (b.p. 107° C. at 3 mm Hg, 92% yield).

¹H NMR (CDCl₃) δ8.40 (s, 1H), 7.60 (d, 1H), 7.12 (d, 1H), 3.15 (t, 1H), 3.00 (t, 1H), 2.56 (s, 3H), 2.40–2.20 (m, 1H), 2.18–2.08 (m, 4H), 2.00–1.92 (m, 1H), 1.80–1.60 (m, 2H).

HClO₄ salt. Anal. calcd. for $C_{11}H_{18}N_2Cl_2O_8$: C, 35.01; H, 4.77; N, 7.42; Cl, 18.83. Found: C, 35.12; H, 4.85; N, 7.37; Cl, 18.76.

N-Ethylcarbamate of (+/−)-6-methylmetanicotine (XVIII)

To a stirred solution of XVII (3.0 g, 0.017 mole) in methylene chloride (25 mL) under nitrogen atmosphere was added dropwise a solution of ethylchloroformate (2.40 g) in methylene chloride (10 mL) at ambient temperature. The mixture was refluxed for 4 hr. After evaporation of solvent on a rotary evaporator under reduced pressure, the resulting oil was vacuum distilled to give XVIII as a thick viscous liquid (b.p. 172°–175° C., 4 mm Hg), which was further purified by silica column chromatography, to yield about 3 g of XVIII (70% yield).

¹H NMR (CDCl₃) δ8.40 (s, 1H), 7.61 (d, 1H), 7.08 (d, 1H), 6.60 (d, 1H), 6.08–6.00 (m, 1H), 4.18 (q, 2H), 3.40 (m, 2H), 2.91 (s, 3H), 2.60–2.42 (m, 5H), 1.22 (t, 3H).

(E)-N-methyl-4-[3-(6-methylpyridin)yl]-3-butene-1-amine (XIX)

Into a round bottom flask was placed XVIII (3.0 g, 0.012 mole), and concentrated hydrochloric acid (15 mL) was added. The mixture was refluxed overnight and the resulting solution basified with aqueous sodium hydroxide (50% w/v) to pH 8–9. The solution was extracted with chloroform (4×25 mL), the combined organic liquors dried over anhydrous sodium carbonate, filtered, and the solvent evaporated to afford an oil. Vacuum distillation of the oil afforded XIX as a clear, colorless liquid (b.p. 80° C. at 0.2 mm Hg, 78% yield). XIX then was provided in the form of a difumarate salt, m.p. 134°–135° C.

Difumarate salt. $^1$H NMR (DMSO-d$_6$) δ8.42 (s, 1H), 7.76 (d, 1H), 7.20 (d, 1H), 6.52–6.24 (m, 6H), 3.00 (t, 2H), 2.60–2.00 (m, 8H).

Anal. Calcd. for $C_{11}H_{16}N_2 \cdot 2C_4H_4O_4$: C, 55.88; H, 5.88; N, 6.86. Found: C, 55.72; H, 5.93; N, 6.83.

Sample No. 7 is N-methyl-(3-pyridinyl)-butane-1-amine, which as prepared essentially in accordance with the following techniques.

(E)-Metanicotine (0.4 g, 2.46 mmole) was dissolved in a mixture of methanol (20 mL) and glacial acetic acid (1 mL) and 5% Pd-C catalyst (30 mg) was added. The mixture was hydrogenated at 50 psig hydrogen for 2 hr. The reaction mixture then was filtered and the solvent removed on a rotary evaporator. To the residue was added water (5 mL) and the aqueous solution basified to pH 8–9 with 40% aqueous sodium hydroxide. The mixture then was extracted with chloroform (5×10 mL), and the combined organic liquors dried over potassium carbonate, filtered and solvent was evaporated under reduced pressure on a rotovaporator. The resulting oil then was provided in the form of a difumarate salt, melting point being 115°–116° C.

Free base. $^1$H NMR (CDCl$_3$) δ8.42 (m, 2H), 7.50 (d, 1H), 7.20 (m, 1H), 2.64–2.58 (m, 4H), 2.40 (s, 3H), 2.78–2.60 (m, 2H), 2.42–2.59 (m, 2H), 1.22 (broad s, 1H).

Difumarate salt. $^1$H NMR (D$_2$O) δ8.64 (d, 2H), 8.43 (d, 1H), 8.00 (m, 1H), 6.62 (s, 4H), 3.24 (t, 2H), 2.90 (t, 2H), 2.70 (s, 3H), 1.81–1.69 (m, 4H).

Anal. calcd. for $C_{10}H_{16}N_2 \cdot 2C_4H_4O_4 \cdot \frac{1}{2}H_2O$: C, 53.33; H, 6.17; N, 6.91. Found: C, 53.33: H, 6.06; N, 7.07.

Sample No. 8 is (E)-metanicotine which was provided generally using the techniques set forth by Laforge, *J.A.C.S.*, Vol. 50, p. 2477 (1928).

For comparison purposes. Sample No. C-1 was provided. This sample is (S)-(–)-nicotine which has been reported to have demonstrated a positive effect towards the treatment of various CNS disorders.

Determination of binding of compounds to relevant receptor sites

Rats (Sprague-Dawley) were maintained on a 12 hour light/dark cycle and were allowed free access to water and food supplied by Wayne Lab Blox, Madison, Wis. Animals used in the present studies weighed 200 to 250 g. Brain membrane preparations were obtained from brain tissue of either males or females.

Rats were killed by decapitation following anesthesia with 70% $CO_2$. Brains were removed and placed on an ice-cold platform. The cerebellum was removed and the remaining tissue was placed in 10 volumes (weight:volume) of ice-cold buffer (Krebs-Ringers HEPES: NaCl, 118 mM; KCl, 4.8 mM; CaCl$_2$, 2.5 mM; MgSO$_4$, 1.2 mM; HEPES, 20 mM; pH to 7.5 with NaOH) and homogenized with a glass-Teflon tissue grinder. The resulting homogenate was centrifuged at 18,000×g for 20 min. and the resulting pellet was resuspended in 20 volumes of water. After 60 min. incubation at 4° C., a new pellet was collected by centrifugation at 18,000×g for 20 min. After resuspension in 10 volumes of buffer, a new final pellet was again collected by centrifugation at 18,000×g for 20 min. Prior to each centrifugation step, the suspension was incubated at 37 ° C. for 5 min. to promote hydrolysis of endogenous acetylcholine. The final pellet was overlayered with buffer and stored at –70 ° C. On the day of the assay, that pellet was thawed, resuspended in buffer and centrifuged at 18,000×g for 20 min. The pellet obtained was resuspended in buffer to a final concentration of approximately 5 mg protein/ml. Protein was determined by the method of Lowry et al., *J. Biol. Chem.*, Vol. 193, pp. 265–275 (1951), using bovine serum albumin as the standard.

The binding of L-[$^3$H]nicotine was measured using a modification of the method of Romano et al., *Science*, Vol. 210, pp. 647–650 (1980) as described previously by Marks et al., *Mol. Pharmacol.*, Vol. 30, pp. 427–436 (1986). The L-[$^3$H]nicotine used in all experiments was purified chromatographically by the method of Romm, et al., *Life Sci.*, Vol. 46, pp. 935–943 (1990). The binding of L-[$^3$H ]nicotine was measured using a 2 hr. incubation at 4° C. Incubations contained about 500 ug of protein and were conducted in 12 mm×75 mm polypropylene test tubes in a final incubation volume of 250 ul. The incubation buffer was Krebs-Ringers HEPES containing 200 mM TRIS buffer, pH 7.5. The binding reaction was terminated by filtration of the protein containing bound ligand onto glass fiber filters (Micro Filtration Systems) that had been soaked in buffer containing 0.5 percent polyethyleneimine. Filtration vacuum was –50 to –100 torr. Each filter was washed five times with 3 ml of ice-cold buffer. The filtration apparatus was cooled to 2° C. before use and was kept cold through the filtration process. Nonspecific binding was determined by inclusion of 10 uM nonradioactive nicotine in the incubations.

The inhibition of L-[$^3$H]nicotine binding by test compounds was determined by including one of eight different concentrations of the test compound in the incubation. Inhibition profiles were measured using 10 nM L-[$^3$H] nicotine and IC$_{50}$ values were estimated as the concentration of compound that inhibited 50 percent of specific L-[$^3$H] nicotine binding. Inhibition constants (Ki values), reported in nM, were calculated from the IC$_{50}$ values using the method of Cheng et al., *Biochem. Pharmacol.*, Vol. 22, pp. 3099–3108 (1973).

Determination of Dopamine Release

Dopamine release was measured by preparing synaptosomes from the striatal area of rat brain obtained from Sprague-Dawley rats generally according to the procedures set forth by Nagy et al., *J. Neurochem.*, Vol. 43, pp. 1114–1123 (1984). Striata from 4 rats were homogenized in 2 ml of 0.32M sucrose buffered with 5 mM HEPES (pH 7.5), using a glass-Teflon tissue grinder. The homogenate was diluted to 5 ml with additional homogenization solution and centrifuged at 1,000×g for 10 min. This procedure was repeated on the new pellet and the resulting superatant was centrifuged at 12,000×g for 20 min. A 3 layer discontinuous Percoll gradient consisting of 16 percent, 10 percent and 7.5 percent Percoll in HEPES-buffered sucrose was made with the final pellet dispersed in the top layer. After centrifugation at 15,000×g for 20 min., the synaptosomes were recovered above the 16 percent layer with a Pasteur pipette, diluted with 8 ml of perfusion buffer (128 mM NaCl, 2.4 mM KCl, 3.2 mM CaCl$_2$, 1.2 mM KH$_2$PO$_4$, 1.2 mM MgSO$_4$, 25 mM HEPES pH 7.4, 10 mM dextrose, 1 mM ascorbate, 0.01 mM pargyline), and centrifuged at 15,000×g for 20 min. The new pellet was collected and re-suspended in perfusion buffer. The synaptosome suspension was incubated for 10 min. at 37° C. [$^3$H]-Dopamine (Amersham, 40–60 Ci/mmol) was added to the suspension to give a final concentration of 0.1 uM, and the suspension was incubated for another 5 min. Using this method, 30 to 90 percent of the dopamine was taken up into the synaptosomes, as determined by scintillation counting following filtration through glass fiber filters soaked with 0.5 percent polyethyleneimine. A continuous perfusion system was used to monitor release following exposure to each ligand. Synaptosomes were loaded onto glass fiber filters (Gelman type A/E). Perfusion buffer was dripped onto the filters (0.2–0.3 ml/min.) and pulled through the filters with a peristaltic pump. Synaptosomes were washed with perfusion buffer for a minimum of 20 min. before addition of the ligand. After the addition of 0.2 ml of a solution containing various concentrations of ligand, the perfusate was collected into scintillation vials at 1 min. intervals and the dopamine released was quantified by scintillation counting. Peaks of radioactivity released above background were summed and the average basal release during that time was subtracted from the total. Release was expressed as a percentage of release obtained with an equal concentration of (S)-(–)-nicotine.

Determination of Log P

Log P values (log octanol/water partition coefficient), which have been used to assess the relative abilities of compounds to pass across the blood-brain barrier (Hansch, et al., *J. Med. Chem.*, Vol. 11, p. 1 (1968)), were calculated according to the methods described by Hopfinger, *Conformational Properties of Macromolecules*, Academic Press (1973) using Cerius$^2$ software package by Molecular Simulations, Inc. for Sample Nos. 1–3, 5–8 and C-1, and Bodor, University of Florida (1991) using the BLogP software package by CAChe Scientific, Inc. for Sample No. 4.

Determination of Interaction with Muscle

Human muscle activation was established on the human clonal line TE67 I/RD which is derived from an embryonal rhabdomyosarcoma (Stratton et al., *Carcinogen*, Vol. 10, pp. 899–905 (1989)). As evidenced through pharmacological (Lukas, *J. Pharmacol. Exp. Ther.*, Vol. 251, pp. 175–182 (1989)), eletrophysiological (Oswald et al, *Neurosci. Lett.*, Vol. 96, pp. 207–212 (1989)), and molecular biological studies (Luther et al., *J. Neurosci.*, Vol. 9, pp. 1082–1096 (1989)) these cells express muscle-like nicotinic receptors. Nicotinic acetylcholine receptor (nAChR) function was assayed using $^{86}Rb^+$ efflux according to a method described by Lukas et al., *Anal. Biochem.*, Vol. 175, pp. 212–218 (1988). Dose-response curves were plotted and the concentration resulting in half maximal activation of specific ion flux through nicotinic receptors determined for human muscle and rat ganglionic preparations (EC50). The maximal activation for individual compounds (Emax) was determined as a percentage of the maximal activation induced by (S)-(–)-nicotine.

Determination of Interaction with Ganglia

Ganglionic effects were established on the rat phcochromocytoma clonal line PC 12, which is a continuous clonal cell line of neural crest origin derived from a tumor of the rat adrenal medulla expressing ganglionic-type neuronal nicotinic receptors (see Whiting et al., *Nature*, Vol. 327, pp. 515–518 (1987); Lukas, *J. Pharmacol. Exp. Ther.*, Vol. 251, pp. 175–182 (1989); Whiting et al., *Mol. Brain Res.*, Vol. 10, pp. 61–70 (1990)). Discussion concerning the heterogeneity of nicotinic receptors subtypes is set forth in Lukas et al., *Internatl. Review Neurobiol.*, Vol. 34, pp. 25–130 (1992). Acetylcholine nicotinic receptors expressed in rat ganglia share a very high degree of homology with their human counterparts. See, Fornasari et al., *Neurosci. Lett.*, Vol. 111, pp. 351–356 (1990) and Chini et al., *Proc. Natl. Acad. Sci. USA*, Vol. 89, pp. 1572–1576 (1992). Both clonal cell lines described above were maintained in proliferative growth phase according to routine protocols (Bencherif et al., *Mol. Cell. Neurosci.*, Vol. 2, pp. 52–65, (1991) and Bencherif et al., *J. Pharmacol. Exp. Ther.*, Vol. 257, pp. 946–953 (1991)). Intact cells on dishes were used for functional studies. Routinely, sample aliquots were reserved for determination of protein concentration using the method of Bradford, *Anal. Biochem.*, Vol. 72, pp. 248–254 (1976) with bovine serum albumin as the standard.

Nicotinic acetylcholine receptor (nAChR) function was assayed using $^{86}Rb^+$ efflux according to a method described by Lukas et al., *Anal. Biochem.*, Vol. 175, pp. 212–218 (1988). Cells were plated in 35-mm diameter wells of 6-well dishes for at least 48 hours and loaded for at least 4 hours at 37° C. in a medium containing serum, and 1 µCi/ml $^{86}Rb^+$. Following removal of the loading medium, cells were quickly washed three times with label-free Ringer's solution and exposed for 4 minutes at 20° C. to 900 µl of Ringer's containing the indicated concentration of compound to be tested (to define total efflux) or in addition to 100 µM methylamine (to define non-specific efflux). The medium was removed and $^{86}Rb^+$ was quantitated using Cerenkov detection (see Lukas et al., *Anal. Blochem.*, Vol. 175, pp. 212–218 (1988)). Specific ion efflux was determined as the difference in isotope efflux between total and non-specific efflux samples. Dose-response curves were plotted and the concentration resulting in half maximal activation of specific ion flux through nicotinic receptors determined for human muscle and rat ganglionic preparations (EC50). The maximal activation for individual compounds (Emax) was determined as a percentage of the maximal activation induced by (S)-(–)-nicotine.

Data are presented in Table I.

TABLE I

| Sample No. | Ki(nM) | logP | Dopamine Release EC50 (nM) | Dopamine Release Emax (% nicotine) | Muscle Effect (% nicotine) | Ganglion Effect (% nicotine) |
|---|---|---|---|---|---|---|
| C-1* | 2 | 0.71 | 115 | 100 | 100 | 100 |
| 1 | 269 | –0.30 | 4360 | 113 | 0 | 0 |
| 2 | 86 | 0.04 | 5800 | 77 | 4 | 1 |
| 3 | 22 | 1.13 | 4000 | 95 | 0 | 0 |
| 4 | 58 | 1.82 | 8350 | 87 | 7 | 59 |
| 5 | 77 | 1.39 | 11339 | 88 | 0 | 0 |
| 6 | 176 | 1.92 | 219 | 60 | 2 | 4 |
| 7 | 910 | 1.51 | ND | 72 | 0 | 31 |
| 8 | 16 | 1.39 | 1470 | 80 | 15 | 0 |

*not an example of the invention
ND = not determined

The data in Table I indicate that the compounds have the capability of passing the blood-brain barrier by virtue of their favorable logP values, binding to high affinity CNS nicotinic receptors as indicated by their low binding constants, and activating CNS nicotinic receptors of a subject and causing neurotransmitter release, thereby demonstrating known nicotinic pharmacology. Thus, the data indicate that such compounds have the capability of being useful in treating CNS disorders involving nicotinic cholinergic systems. Furthermore, the data indicate that the compounds do not cause any appreciable effects at muscle sites and ganglionic sites, thus indicating a lack of undesirable side effects in subjects receiving administration of those compounds.

What is claimed is:

1. A compound, (E)-N-methyl-4-(3-(6-methylpyridin)yl)-3-butene-1-amine.

2. A compound having the formula:

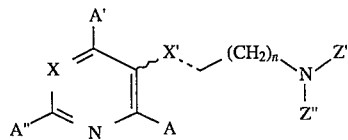

where X is nitrogen or carbon bonded to a substituent species wherein that species has a sigma m value of less than 0 to about −0.3 and greater than 0 to about 0.75;

n is an integer which ranges from 1 to 5; Z' and Z" individually represent hydrogen or alkyl containing one to five carbon atoms; A and A' represent hydrogen; A" represents hydrogen, methyl or ethyl; the dashed line in the structure represents a C—C triple bond; the wavy line in the structure represents C—C single bond; and X' represents C.

3. The compound of claim 2 wherein X is C—H; n is 2; A, A', A" and Z' each are hydrogen; and Z" is hydrogen or methyl.

4. The compound of claim 2 wherein the compound is N-methyl-4-(3-pyridinyl)-3-butyne-1-amine.

5. A compound having the formula:

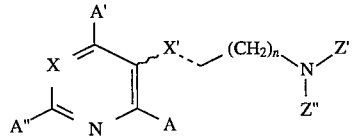

where X is nitrogen or carbon bonded to a substituent wherein that species has a sigma m value between about −0.3 and about 0.75; n is 2 or 3; Z' and Z" individually represent hydrogen or alkyl containing one to five carbon atoms; A and A' represent hydrogen; A" represents hydrogen, methyl or ethyl; the dashed line in the structure represents a C—C triple bond; the wavy line in the structure represents C—C single bond; and X' represents C.

6. The compound of claim 2 wherein n is 2 or 3.

* * * * *